United States Patent
Polonka et al.

(10) Patent No.: US 7,476,395 B2
(45) Date of Patent: Jan. 13, 2009

(54) COSMETIC COMPOSITION WITH SOFT FOCUS PROPERTIES

(75) Inventors: Jack Polonka, Peekskill, NY (US); Katherine Mary Rosevear, Wallingford, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 11/615,129

(22) Filed: Dec. 22, 2006

(65) Prior Publication Data

US 2007/0237730 A1    Oct. 11, 2007

Related U.S. Application Data

(60) Provisional application No. 60/744,623, filed on Apr. 11, 2006.

(51) Int. Cl.
  *A61K 7/42* (2006.01)
  *A61K 8/00* (2006.01)

(52) U.S. Cl. .................. 424/401; 424/401; 424/69

(58) Field of Classification Search .................. None
See application file for complete search history.

(56) References Cited

U.S. PATENT DOCUMENTS

| | | | |
|---|---|---|---|
| 5,256,404 A | 10/1993 | Martino et al. | |
| 5,972,359 A | 10/1999 | Sine et al. | |
| 5,997,890 A | 12/1999 | Sine et al. | |
| 6,174,533 B1 | 1/2001 | SaNogueira, Jr. et al. | |
| 6,248,338 B1 | 6/2001 | Muller et al. | |
| 6,299,907 B1* | 10/2001 | Seib et al. | 424/499 |
| 6,903,057 B1 | 6/2005 | Tsaur | |
| 7,037,512 B2 | 5/2006 | Perricone | |
| 2002/0176833 A1* | 11/2002 | Nagatani et al. | 424/63 |
| 2005/0079190 A1 | 4/2005 | Polonka | |
| 2005/0163730 A1 | 7/2005 | Rosevear et al. | |
| 2005/0163813 A1 | 7/2005 | Kosbach et al. | |
| 2005/0249684 A1 | 11/2005 | Dobkowski et al. | |
| 2005/0255058 A1 | 11/2005 | Kroepke et al. | |
| 2005/0271607 A1 | 12/2005 | Perricone | |
| 2006/0018939 A1 | 1/2006 | Bazin et al. | |
| 2006/0045890 A1 | 3/2006 | Gonzalez et al. | |
| 2007/0020208 A1 | 1/2007 | Gutkowski et al. | |

FOREIGN PATENT DOCUMENTS

| | | |
|---|---|---|
| EP | 0 213 953 | 9/1986 |
| WO | 2005/110355 A2 | 11/2005 |
| WO | 2005/110356 A1 | 11/2005 |

OTHER PUBLICATIONS

SpectrAl PC-401—Cabot Corporation—Jan. 2004.
Alusion—A natural soft focus brochure—2004.

* cited by examiner

*Primary Examiner*—Sreeni Padmanabhan
*Assistant Examiner*—Layla Soroush
(74) *Attorney, Agent, or Firm*—Milton L. Honig

(57) ABSTRACT

A cosmetic composition is provided to achieve a soft focus effect. Imperfections in skin complexion can be hidden. The composition includes a water-insoluble partially hydrated granular starch having an average particle size ranging from about 500 to about 10,000 nm, a spherical alumina having a refractive index from 1.6 to 1.9 and average particle size from about 5 to about 300 nm, an inorganic material in flat, platy form having an average particle size ranging from about 0.1 to about 30 micron and a cosmetically acceptable carrier.

12 Claims, No Drawings

COSMETIC COMPOSITION WITH SOFT FOCUS PROPERTIES

BACKGROUND OF THE INVENTION

1. Field of the Invention

The invention relates to compositions for improving the appearance of skin, particularly to provide good coverage over imperfections such as pores and uneven skin tone, while retaining a natural skin appearance.

2. The Related Art

A matte effect is often sought from facially applied cosmetics. The matte finish overcomes the shiny effect engendered by greasy skin, particularly under hot and humid conditions. Absorbent fillers such as talc, silica, kaolin and other inorganic particulates have been used to achieve the effect by their optical properties.

Imperfect skin can be hidden in two ways through manipulation of light transmission. In the first, components of the cosmetic may simply reflect light back toward the source. An alternative approach is referred to as achieving a soft focus effect. Here the incoming light is distorted by scattering (lensing). Components of the color cosmetic in this mechanism operate as lenses to bend and twist light into a variety of directions.

While it is desirable to hide imperfect skin through a matte effect, there is also a desire to achieve a healthy skin radiance. A cosmetic covering that is too opaque hides the skin under a paint-like coating. Imperfections are hidden but there is no radiance. Some refer to this as whitening. Where light transmission is insufficiently hindered, the opposite occurs. Here the glow may be healthy but aesthetically displeasing skin topography and color may now be apparent.

U.S. Pat. No. 5,997,890 (Sine et al.), U.S. Pat. No. 5,972,359 (Sine et al.), and U.S. Pat. No. 6,174,533 B1 (SaNogueira, Jr.) are all directed to topical compositions to provide good coverage of skin imperfections. The solution proposed by these documents is the use of a metal oxide with a refractive index of at least about 2 and a neat primary particle size of from about 100 to about 300 nm. Preferred particulates are titanium dioxide, zirconium oxide and zinc oxide.

A significant disadvantage of titanium dioxide and zinc oxide is the whitening effect upon the skin. An undesirable ashen appearance is unfortunately created.

U.S. patent application Ser. No. 2005/0163813 A1 (Kosbach et al.) reports use of fumed alumina particles for enhancing the soft-focus effect of certain cosmetic compositions. Levels of at least 3% are required to accomplish effective light diffusing properties to disguise skin imperfections.

Crosslinked silicone elastomers have been identified as aids in achieving soft focus. U.S. patent application Ser. No. 2005/0163730 A1 (Rosevear et al.) discloses a synergistic interaction between crosslinked silicone elastomer and zinc oxide having average particle size less than 300 nm. A related disclosure is found in U.S. patent application Ser. No. 2005/0249684 A1 (Dobkowski et al.) wherein a taurate polymer enhances optical effects in combination with a silicone elastomer and zinc oxide.

A disadvantage of silicone elastomers is their incompatibility with water. These materials are also difficult to disperse within aqueous emulsions at relatively high concentration levels of the elastomer.

Therefore, the challenge remains to provide a soft focus effect which avoids the whitening phenomena and also has good compatibility with water or at least water and oil emulsions.

SUMMARY OF THE INVENTION

A cosmetic composition is provided which includes:
(i) from about 0.1 to about 20% by weight of a water-insoluble partially hydrated granular starch with average particle size ranging from about 500 to about 10,000 nm;
(ii) from about 0.1 to about 15% by weight of alumina having an average particle size ranging from about 5 to about 300 nm and refractive index from 1.6 to 1.9;
(iii) from about 0.01 to about 5% by weight of an inorganic material in flat, platy form with average particle size ranging from about 0.1 to about 30 micron; and
(iv) a cosmetically acceptable carrier.

DETAILED DESCRIPTION OF THE INVENTION

Now it has been observed that a soft focus effect can be obtained by combination of fine particle size spherical alumina (especially fumed alumina), a water-insoluble partially hydrated starch of average particle size ranging from about 500 to about 10,000 nm, and an inorganic material in flat platy form. Each of these materials interacts to achieve a desired soft focus effect.

Alumina

An important component of the present invention is a spherical alumina. By spherical is meant a generally round although not a smooth sphere. This material should be a powder of average particle size ranging from about 5 to about 300 nm. More preferably, the average particle size should range from about 15 to 295 nm, still more preferably from about 100 to about 250 nm, and optimally from about 120 to about 250 nm.

Further, spherical alumina of this invention should have a refractive index ranging from 1.6 to 1.9, preferably from 1.65 to 1.85, optimally from 1.70 to 1.80.

Alumina useful in the present invention can be coated or uncoated. Most preferably the particles are uncoated powders and have a positive surface charge. Fumed alumina is especially effective. Commercially the material is available as SpectrAl™ PC-401 sold by the Cabot Corporation. This material has an Oil Absorption of 48 g/100 g oil, a bulk density of 8.0 lb/ft$^3$ maximum, a specific gravity of 3.6 g/cm$^3$ and a refractive index of 1.77.

Amounts of the spherical alumina suitable for the present invention may range from about 0.1 to about 15% even more preferably from about 0.5 to about 6%, still more preferably from about 0.5 to less than about 3%, optimally from about 1 to 2.5% by weight of the composition.

Water-Insoluble Partially Hydrated Starch Granulate

Another important component of the present invention is a water-insoluble partially hydrated granular starch having an average particle size ranging from about 500 to about 10,000 nm, preferably from about 1,000 to about 9,000 nm, optimally from about 3,000 to about 8,000 nm. Advantageously, the starch can have a refractive index from about 1.35 to about 1.45, preferably from about 1.38 to about 1.42.

Starches of the present invention may include but are not limited to those derived from any plant source including corn, potato, rice, wheat, tapioca, waxy maize and high amylase corn. Tapioca is most preferred. Amounts of the partially hydrated granular starch may range from about 0.1 to about 20%, preferably from about 0.5 to about 10%, optimally from about 1 to about 3% by weight.

Partially hydrated starches of the present invention are achieved by heating starch in water to 50° C. and holding this temperature for from about 0.5 to about 4 hours, preferably from about 1 to about 2 hours. In the preferred embodiment, a 10% starch is heated in 90% water to 50° C. for one hour. Partially hydrated starch particles created in this manner are then added to other components of the cosmetic compositions. Care should be taken to avoid heating the compositions now formulated with the starch particles to temperatures in excess of above 50° C.

Levels of hydration may range from 5 to 80%, preferably from 10 to 50%, and optimally from 15 to 35% by weight of complete hydration of the starch.

Inorganic Flaty Platy Material

A still further component of the present invention is an inorganic material in flat, platy form. The term flat, platy means one size dimension is longer than another. Advantageously these materials will have an index of refraction ranging from about 1.6 to about 2.7, particularly from 1.85 to 2.7 optimally from 1.90 to 2.7 Average particle sizes can range from about 0.1 to about 30 micron, preferably from about 0.1 to about 20 micron, more preferably from about 0.1 to 18 micron, and optimally from 5 to 18 micron. Suitable materials include bismuth oxychloride, aluminum oxide, barium sulfate, boron nitride, zirconium oxide and mica. Particularly useful are titanium dioxide coated micas, most especially those with average particle sizes less than 20 micron. Illustrative of these particles is a material called Prespearls Smooth Satin Silver™ which is titanium dioxide (Cl 77891) coated mica (Cl 77019) available from the Presperse Corporation. Another example of a suitable material is aluminum oxide sold under the trademark Alusion® Powder (AL 5-10) available from the APT Corporation having mean particle size from 5 to 10 micron. Further details on these materials can be found in U.S. patent application No. 2005/0079190 A1 (Polonka) herein incorporated by reference. Amounts of the flat, platy material may range from about 0.01 to about 5%, preferably from about 0.1 to about 3%, optimally from about 0.5 to about 1.5% by weight of the composition.

Carrier

A variety of other components may be present in the compositions of the present invention Foremost is that of water which serves as a carrier. Amounts of water may range from about 1 to about 90%, preferably from about 30 to about 80%, optimally from about 50 to about 80% by weight of the composition.

Emollient materials may be included as carriers in compositions of this invention. These may be in the form of silicone oils, synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature (20-25° C). Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to $0.1 \, m^2/s$ at 25° C. Among the preferred nonvolatile emollients useful in the present compositions are the polydimethyl siloxanes having viscosities from about $1 \times 10^{-5}$ to about $4 \times 10^{-4}$ $m^2/s$ at 25° C.

Among the ester emollients are:

a) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

b) Ether-esters such as fatty acid esters of ethoxylated fatty alcohols.

c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

d) Wax esters such as beeswax, spermaceti wax and tribehenin wax.

e) Sterols esters, of which cholesterol fatty acid esters are examples thereof.

f) Sugar ester of fatty acids such as sucrose polybehenate and sucrose polycottonseedate.

Hydrocarbons which are suitable cosmetically acceptable carriers include petrolatum, mineral oil, $C_{11}$-$C_{13}$ isoparaffins, polyalphaolefins, and especially isohexadecane, available commercially as Permethyl 101A from Presperse Inc.

Humectants of the polyhydric alcohol-type can be employed as cosmetically acceptable carriers. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. The amount of humectant may range anywhere from 0.5 to 50%, preferably between 1 and 15% by weight of the composition. Most preferred is glycerol (also known as glycerin). Amounts of glycerin may range from about 1% to about 50%, preferably from 10 to 35%, optimally from 15 to 30% by weight of the composition.

Optional Components

Sunscreen actives may also be included in compositions of the present invention. These will be organic compounds having at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane). Particularly useful are: 2-ethylhexyl p-methoxycinnamate, 4,4'-t-butyl methoxydibenzoylmethane, 2-hydroxy-4-methoxybenzophenone, octyidimethyl p-aminobenzoic acid, digalloyltrioleate, 2,2-dihydroxy-4-methoxybenzophenone, ethyl 4-[bis (hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Particularly preferred are such materials as ethylhexyl p-methoxycinnamate, available as Parsol MCX®, Avobenzene, available as Parsol 1789®, and Dermablock OS® (octylsalicylate).

Amounts of the organic sunscreen agent will range from about 0.1 to about 15%, preferably from about 0.5% to about 10%, optimally from about 1% to about 8% by weight of the composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain vitamins and flavanoids. Illustrative water-soluble vitamins are Niacinamide, Vitamin $B_2$, Vitamin $B_6$, Vitamin C and Biotin. Among the useful water-insoluble vitamins are Vitamin A (retinol), Vitamin A Palmitate, ascorbyl tetraisopalmitate, Vitamin E (tocopherol), Vitamin E Acetate and DL-panthenol. A particularly suitable Vitamin $B_6$ derivative is Pyridoxine Palmitate. Among the preferred flavanoids are glucosyl hesperidin and rutin. Total amount of vitamins or flavanoids when present in compositions according to the present invention may range from 0.001 to 10%, preferably from 0.01% to 1%, optimally from 0.1 to 0.5% by weight of the composition.

Desquamation agents are further optional components. Illustrative are the alpha-hydroxycarboxylic acids and beta-hydroxycarboxylic acids and salts of these acids. Among the former are salts of glycolic acid, lactic acid and malic acid. Salicylic acid is representative of the beta-hydroxycarboxylic acids. Amounts of these materials when present may range from about 0.1 to about 15% by weight of the composition.

A variety of herbal extracts may optionally be included in compositions of this invention. Illustrative are pomegranate, white birch (*Betula Alba*), green tea, chamomile, licorice and extract combinations thereof. The extracts may either be water soluble or water-insoluble carried in a solvent which respectively is hydrophilic or hydrophobic. Water and ethanol are the preferred extract solvents.

Compositions of the present invention which are aqueous may but not necessarily have a pH ranging from about 2 to about 6.8, preferably from about 3 to about 5.5.

A small amount of emulsifying surfactant may be present. Surfactants may be anionic, nonionic, cationic, amphoteric and mixtures thereof. Levels may range from 0.1 to 5%, preferably from 0.1 to 2%, optimally from 0.1 to 1% by weight. Advantageously the amount of surfactant present should not be sufficient for lather formation. In these instances, less than 2% by weight, preferably less than 1%, and optimally less than 0.5% by weight surfactant is present.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLES 1-8

A series of cosmetic compositions having soft focus effect according to the present invention are presented in the Table below.

| Ingredient | Example (Weight %) | | | | | | | |
|---|---|---|---|---|---|---|---|---|
| | 1 | 2 | 3 | 4 | 5 | 6 | 7 | 8 |
| Water | qs | qs | qs | qs | qs | qs | qs | qs |
| Lactic Acid/Potassium Lactate | 8.000 | 8.000 | 8.000 | 8.000 | 8.000 | 8.000 | 8.000 | 8.000 |
| Glycerin | 15.000 | 5.000 | 15.000 | 3.000 | 3.000 | 4.000 | 1.000 | 5.000 |
| Dimethicone 50 cst. | 6.000 | 4.000 | 4.000 | 6.000 | 2.000 | 2.000 | 1.000 | 4.000 |
| Mineral Oil | 2.000 | 3.000 | 3.000 | 2.000 | 1.000 | 2.000 | 1.000 | 2.000 |

-continued

| Ingredient | Example (Weight %) | | | | | | | |
|---|---|---|---|---|---|---|---|---|
| | 1 | 2 | 3 | 4 | 5 | 6 | 7 | 8 |
| Stearic Acid | 2.920 | 2.920 | 2.920 | 2.920 | 2.920 | 2.920 | 2.920 | 2.920 |
| Glycol Stearate/Stearamide AMP | 1.730 | 1.730 | 1.730 | 1.730 | 1.730 | 1.730 | 1.730 | 1.730 |
| PEG-100 Stearate | 1.480 | 1.480 | 1.480 | 1.480 | 1.480 | 1.480 | 1.480 | 1.480 |
| Tapioca Starch | 0.500 | 1.500 | 0.500 | 2.500 | 2.500 | 2.000 | 2.000 | 3.500 |
| Ethylhexyl Methoxycinnamate | 1.250 | 1.250 | 2.000 | 2.000 | 1.000 | 2.000 | 4.000 | 5.000 |
| Smooth Satin Silver Pigment (Titanium Dioxide Coated Mica) | 1.000 | 1.000 | 1.000 | 2.000 | 0.500 | 1.000 | 1.000 | 1.000 |
| SpectrAl 51 ™ (Alumina) | 1.500 | 1.000 | 1.500 | 2.000 | 2.000 | 0.250 | 3.000 | 0.500 |
| Glyceryl Monostearate | 0.810 | 0.810 | 0.810 | 0.810 | 0.810 | 0.810 | 0.810 | 0.810 |
| Cetyl Alcohol | 0.460 | 0.460 | 0.460 | 0.460 | 0.460 | 0.460 | 0.460 | 0.460 |
| Magnesium aluminum Silicate | 0.300 | 0.300 | 0.300 | 0.300 | 0.300 | 0.300 | 0.300 | 0.300 |
| Fragrance | 0.150 | 0.150 | 0.150 | 0.150 | 0.150 | 0.150 | 0.150 | 0.150 |
| Petrolatum | 0.100 | 0.100 | 0.100 | 0.100 | 0.100 | 0.100 | 0.100 | 0.100 |
| Glydant Plus ® | 0.100 | 0.100 | 0.100 | 0.100 | 0.100 | 0.100 | 0.100 | 0.100 |
| Xanthan Gum | 0.050 | 0.050 | 0.050 | 0.050 | 0.050 | 0.050 | 0.050 | 0.050 |
| Disodium EDTA | 0.050 | 0.050 | 0.050 | 0.050 | 0.050 | 0.050 | 0.050 | 0.050 |
| Generol 122 ® (Soy Sterol) | 0.020 | 0.020 | 0.020 | 0.020 | 0.020 | 0.020 | 0.020 | 0.020 |
| Vitamin A Palmitate | 0.017 | 0.017 | 0.017 | 0.017 | 0.017 | 0.017 | 0.017 | 0.017 |
| Vitamin E Acetate | 0.010 | 0.010 | 0.010 | 0.010 | 0.010 | 0.010 | 0.010 | 0.010 |
| Sunflower Seed Oil | 0.010 | 0.010 | 0.010 | 0.010 | 0.010 | 0.010 | 0.010 | 0.010 |
| Lecithin | 0.010 | 0.010 | 0.010 | 0.010 | 0.010 | 0.010 | 0.010 | 0.010 |
| Sodium Stearoyl Lactylate | 0.001 | 0.001 | 0.001 | 0.001 | 0.001 | 0.001 | 0.001 | 0.001 |

EXAMPLE 9

Experiments were conducted to evaluate the optical property contributions of hydrated tapioca starch, spherical alumina and flat platy inorganic materials. The base formula is outlined in Table I below.

TABLE I

| INGREDIENT | SAMPLE (WEIGHT %) | | | | | | | | | |
|---|---|---|---|---|---|---|---|---|---|---|
| | 9.1 | 9.2 | 9.3 | 9.4 | 9.5 | 9.6 | 9.7 | 9.8 | 9.9 | 9.10 |
| Water | qs | qs | qs | qs | qs | qs | qs | qs | qs | qs |
| Lactic Acid/Potassium Lactate | 8.000 | 8.000 | 8.000 | 8.000 | 8.000 | 8.000 | 8.000 | 8.000 | 8.000 | 8.000 |
| Glycerin | 5.000 | 5.000 | 5.000 | 5.000 | 5.000 | 5.000 | 5.000 | 5.000 | 5.000 | 5.000 |
| Dimethicone 50 cst. | 4.000 | 4.000 | 4.000 | 4.000 | 4.000 | 4.000 | 4.000 | 4.000 | 4.000 | 4.000 |
| Mineral Oil | 3.000 | 3.000 | 3.000 | 3.000 | 3.000 | 3.000 | 3.000 | 3.000 | 3.000 | 3.000 |
| Stearic Acid | 2.920 | 2.920 | 2.920 | 2.920 | 2.920 | 2.920 | 2.920 | 2.920 | 2.920 | 2.920 |
| Glycol Stearate/Stearamide AMP | 1.730 | 1.730 | 1.730 | 1.730 | 1.730 | 1.730 | 1.730 | 1.730 | 1.730 | 1.730 |
| PEG-100 Stearate | 1.480 | 1.480 | 1.480 | 1.480 | 1.480 | 1.480 | 1.480 | 1.480 | 1.480 | 1.480 |
| Ethylhexyl Methoxycinnamate | 1.250 | 1.250 | 1.250 | 1.250 | 1.250 | 1.250 | 1.250 | 1.250 | 1.250 | 1.250 |
| Tapioca Starch (1 μm) | 1.500 | 0.500 | 1.500 | 1.500 | 1.500 | 1.500 | 1.500 | 1.500 | — | — |
| Silicone Elastomer DC 9509 | — | 0.400 | — | — | 0.400 | — | — | — | — | — |
| Partially Hydrated Cornstarch (B990) (10 μm) | — | 1.500 | — | — | 0.500 | — | — | — | — | — |
| Cornstarch Fully Hydrated (100 μM) | — | — | — | — | — | — | — | — | — | 1.500 |
| Smooth Satin Silver Pigment (Titanium Dioxide Coated Flat Platy Mica) | 1.000 | — | 1.000 | — | 1.000 | — | — | — | — | 1.000 |
| Spherical Alumina (15 nm) | 1.000 | — | — | — | — | — | — | — | — | — |
| Spherical Alumina (150 nm) | — | — | 1.000 | 1.000 | — | — | — | 1.000 | — | 1.000 |
| Spherical Alumina (18 μm) | — | — | — | — | 1.000 | — | — | 1.000 | — | — |
| Flat Platy Alumina (9 μm) | — | — | — | — | — | — | 1.000 | 1.000 | 1.000 | — |

TABLE I-continued

| INGREDIENT | SAMPLE (WEIGHT %) | | | | | | | | | |
|---|---|---|---|---|---|---|---|---|---|---|
| | 9.1 | 9.2 | 9.3 | 9.4 | 9.5 | 9.6 | 9.7 | 9.8 | 9.9 | 9.10 |
| Glyceryl Monostearate | 0.810 | 0.810 | 0.810 | 0.810 | 0.810 | 0.810 | 0.810 | 0.810 | 0.810 | 0.810 |
| Cetyl Alcohol | 0.460 | 0.460 | 0.460 | 0.460 | 0.460 | 0.460 | 0.460 | 0.460 | 0.460 | 0.460 |
| Magnesium aluminum Silicate | 0.300 | 0.300 | 0.300 | 0.300 | 0.300 | 0.300 | 0.300 | 0.300 | 0.300 | 0.300 |
| Fragrance | 0.150 | 0.150 | 0.150 | 0.150 | 0.150 | 0.150 | 0.150 | 0.150 | 0.150 | 0.150 |
| Petrolatum | 0.100 | 0.100 | 0.100 | 0.100 | 0.100 | 0.100 | 0.100 | 0.100 | 0.100 | 0.100 |
| Glydant Plus ® | 0.100 | 0.100 | 0.100 | 0.100 | 0.100 | 0.100 | 0.100 | 0.100 | 0.100 | 0.100 |
| Xanthan Gum | 0.050 | 0.050 | 0.050 | 0.050 | 0.050 | 0.050 | 0.050 | 0.050 | 0.050 | 0.050 |
| Disodium EDTA | 0.050 | 0.050 | 0.050 | 0.050 | 0.050 | 0.050 | 0.050 | 0.050 | 0.050 | 0.050 |
| Generol 122 ® (Soy Sterol) | 0.020 | 0.020 | 0.020 | 0.020 | 0.020 | 0.020 | 0.020 | 0.020 | 0.020 | 0.020 |
| Vitamin A Palmitate | 0.017 | 0.017 | 0.017 | 0.017 | 0.017 | 0.017 | 0.017 | 0.017 | 0.017 | 0.017 |
| Vitamin E Acetate | 0.010 | 0.010 | 0.010 | 0.010 | 0.010 | 0.010 | 0.010 | 0.010 | 0.010 | 0.010 |
| Sunflower Seed Oil | 0.010 | 0.010 | 0.010 | 0.010 | 0.010 | 0.010 | 0.010 | 0.010 | 0.010 | 0.010 |
| Lecithin | 0.010 | 0.010 | 0.010 | 0.010 | 0.010 | 0.010 | 0.010 | 0.010 | 0.010 | 0.010 |
| Sodium Stearoyl Lactylate | 0.001 | 0.001 | 0.001 | 0.001 | 0.001 | 0.001 | 0.001 | 0.001 | 0.001 | 0.001 |

Optical Measurements

Opacity is the measure of intensity attenuation of a transmitted light beam shone perpendicular to a medium or film. The higher the direct beam attenuation, the greater will be the opacity. The source of the light beam attenuation is two fold: A) Some of the original light is reflected back from the film/medium. This gives the film/medium a true white/opaque appearance with great hiding power. Using pigment-grade $TiO_2$ in a formulation will give the effect. B) Some of the light is deflected from the straight beam path but still transmitted through the film/medium. In effect, the film/medium goes from being transparent to translucent, creating a "blurred" image. Another term for this is soft focus.

Procedure: Apply (or draw down) a 3 mil (76.2 μm) film of a formulation using a draw down bar on to a plastic overhead transparency sheet. Let the film dry for 2 hours at room temperature. Take the coated overhead transparency and place it in an Instrument Systems goniospectrophotometer. Set the light source and detector arrayed in a straight line perpendicular to the coated transparency. The light source (set at 209 million Watt-nm/cm², which serves as a reference for all Transmission Intensity Values reported herein) is turned on and the measurement of the transmitted light intensity is made. Further measurements are made by moving the detector 10, 30, 40, 50 degrees away from the direct transmission normal. These values indicate the extent of soft focus light scattering. The Reflectance or "radiance" of a product is determined in the same way as opacity/soft focus light scattering, except for the positions of the light source and detector. The detector is 30 degrees on one side of the normal/perpendicular, while the light source is 20 degrees on the other side. To determine the extent of the intensity attenuation, compare the intensity value to that of an uncoated overhead transparency. The difference between these two values is the extent of the attenuation or opacity.

Results: The effect of certain components on the optical properties of the compositions was evaluated by testing formulations with those components removed. Results are reported in Table II. The Acceptability range values relate to body rather than face areas. Numbers in bold are values found outside the Acceptability Transmission Intensity range.

TABLE II

| | Sample No. (Watt-nm/cm²) | | | | | | | | | | Acceptability Transmission Intensity (Watt-nm/cm²) |
|---|---|---|---|---|---|---|---|---|---|---|---|
| Transmission Angle in degrees | 9.1 | 9.2 | 9.3 | 9.4 | 9.5 | 9.6 | 9.7 | 9.8 | 9.9 | 9.10 | |
| 0 | 8.48 M | 20.14 M | 8.23 M | 17.71 M | 20.37 M | 16.89 M | 18.18 M | 10.45 M | 22.38 M | 17.12 M | 6 to 10 million |
| 10 | 1.85 M | 1.60 M | 1.83 M | 1.86 M | 1.62 M | 1.61 M | 1.67 M | 1.73 M | 1.42 M | 1.71 M | 1 to 2 million |
| 30 | 98.86 K | 58.00 K | 110.46 K | 71.59 K | 60.04 K | 62.10 K | 93.92 K | 115.38 K | 45.03 K | 83.25 K | 90 to 140 thousand |
| 40 | 59.41 K | 22.10 K | 65.29 K | 34.59 K | 19.93 K | 23.69 K | 55.45 K | 70.31 K | 19.21 K | 45.22 K | 50 to 80 thousand |
| 50 | 35.15 K | 11.72 K | 41.07 K | 23.18 K | 10.72 K | 12.57 K | 28.16 K | 42.21 K | 10.88 K | 25.73 K | 30 to 60 thousand |

TABLE II-continued

| | Sample No. (Watt-nm/cm$^2$) | | | | | | | | | | Acceptability Transmission Intensity (Watt-nm/cm$^2$) |
|---|---|---|---|---|---|---|---|---|---|---|---|
| | 9.1 | 9.2 | 9.3 | 9.4 | 9.5 | 9.6 | 9.7 | 9.8 | 9.9 | 9.10 | |
| Reflection Angle in degrees | | | | | | | | | | | |
| 20 | 176. K | 195 K | 190.4 K | 206.3 K | 200 K | 224.1 K | 282.8 K | 200.2 K | 426.8 K | 336.7 K | |
| 30 | 124.7 K | 100.1 K | 137.7 K | 104.0 K | 101.3 K | 112.1 K | 130.1 K | 111.7 K | 155.9 K | 210.2 K | 100 to 170 thousand |

Samples 9.1 and 9.3 provided the best performance and are representative of a preferred embodiment of the present invention. Transmission Intensity (Opacity) at all measured angles and Reflection Intensity for these formulas fell within the parameters necessary to achieve both soft focus and radiance. Sample 9.2 formulated without any spherical alumina and without any flat platy inorganic material does not provide an adequate result. Sample 9.4 differs from 9.3 by lacking the flat platy inorganic material; the formula does not achieve maximum soft focus efficiency. In Sample 9.5, the alumina is too large for proper soft focus. Sample 9.6 lacks spherical alumina and flat platy inorganic material. Sample 9.7 lacks the spherical alumina. Both Samples 9.6 and 9.7 do not possess all optical parameters within the acceptable Transmission Intensity. Sample 9.8 provides an optical response within the optimum transmission/reflection parameters. Sample 9.9 lacks both the hydrated granular starch and the spherical alumina; this formula lies outside the acceptable transmission parameters. Sample 9.10 replaces partially hydrated granular starch with a totally cooked starch (average particle size greater than 100 μm) resulting in a formula which does not meet acceptable transmission intensity levels.

What is claimed is:

1. A cosmetic composition comprising:
   (i) from about 0.1 to about 20% by weight of a water-insoluble partially hydrated granular starch with average particle size ranging from about 500 to about 10,000 nm;
   (ii) from about 0.1 to about 15% by weight of a spherical alumina having an average particle size ranging from about 5 to about 300 nm and refractive index from 1.6 to 1.9;
   (iii) from about 0.01 to about 5% by weight of an inorganic material in flat platy form with average particle size ranging from about 0.1 to about 30 micron; and
   (iv) a cosmetically acceptable carrier.

2. The composition according to claim 1 wherein the inorganic material is mica coated with titanium dioxide.

3. The composition according to claim 1 wherein the alumina is non-coated.

4. The composition according to claim 1 having a pH ranging from about 2 to about 6.8.

5. The composition according to claim 1 having a pH ranging from about 3 to about 5.5.

6. The composition according to claim 1 wherein the starch is a tapioca starch.

7. The composition according to claim 1 wherein the starch has an average particle size ranging from about 3000 to about 8000 nm.

8. The composition according to claim 1 wherein the alumina is present in an amount ranging from about 0.5 to less than about 3% by weight.

9. The composition according to claim 1 wherein the alumina is present in an amount ranging from 0.5 to 2.5% by weight.

10. The composition according to claim 1 wherein the partially hydrated granular starch is present in an amount from about 0.5 to about 10% by weight.

11. The composition according to claim 1 wherein the inorganic material is a flat platy single crystal aluminum oxide.

12. The composition according to claim 1 wherein the inorganic material is a flat platy barium sulfate.

* * * * *

UNITED STATES PATENT AND TRADEMARK OFFICE
CERTIFICATE OF CORRECTION

PATENT NO.       : 7,476,395 B2
APPLICATION NO.  : 11/615129
DATED            : January 13, 2009
INVENTOR(S)      : Polonka et al.

It is certified that error appears in the above-identified patent and that said Letters Patent is hereby corrected as shown below:

On the title page item (73), "Conopco, Inc., Englewood Cliffs, NJ" should read
-- Conopco, Inc., d/b/a Unilever, Englewood Cliffs, NJ --.

Signed and Sealed this

Twenty-fourth Day of February, 2009

JOHN DOLL
*Acting Director of the United States Patent and Trademark Office*